(12) United States Patent
Hakkens et al.

(10) Patent No.: US 11,253,232 B2
(45) Date of Patent: Feb. 22, 2022

(54) ULTRASOUND DEVICE CONTACTING

(71) Applicant: KONINKLIJKE PHILIPS N.V., Eindhoven (NL)

(72) Inventors: Franciscus Johannes Gerardus Hakkens, Eersel (NL); Harm Jan Willem Belt, Weert (NL); Mark Thomas Johnson, Arendonk (NL); Daan Anton Van Den Ende, Breda (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 232 days.

(21) Appl. No.: 16/348,217

(22) PCT Filed: Nov. 8, 2017

(86) PCT No.: PCT/EP2017/078518
§ 371 (c)(1),
(2) Date: May 8, 2019

(87) PCT Pub. No.: WO2018/091317
PCT Pub. Date: May 24, 2018

(65) Prior Publication Data
US 2019/0321007 A1      Oct. 24, 2019

(30) Foreign Application Priority Data
Nov. 15, 2016  (EP) ..................................... 16198779

(51) Int. Cl.
*A61B 8/00*       (2006.01)
(52) U.S. Cl.
CPC .............. *A61B 8/54* (2013.01); *A61B 8/4455* (2013.01); *A61B 8/4483* (2013.01)

(58) Field of Classification Search
CPC ....... A61B 8/54; A61B 8/4455; A61B 8/4483; A61B 8/58; A61B 8/4444; A61B 8/429
See application file for complete search history.

(56) References Cited

U.S. PATENT DOCUMENTS

| | | | |
|---|---|---|---|
| 5,997,479 A | 12/1999 | Savord et al. | |
| 6,013,032 A | 1/2000 | Savord | |

(Continued)

FOREIGN PATENT DOCUMENTS

| | | |
|---|---|---|
| EP | 1415596 A1 | 5/2004 |
| JP | S61-240800 A | 10/1986 |
| WO | 2017186781 A1 | 11/2017 |

OTHER PUBLICATIONS

M.Knite and J.Zavickis (2009). Prospective Polymer Composite Materials for Applications in Flexible Tactile Sensors, Contemporary Robotics—Challenges and Solutions, A D Rodi (Ed.), ISBN: 978-953-307-038-4, InTech, Available from: http://www.intechopen.com/books/contemporary-robotics-challenges-andsolutions/prospective-polymer-composite-materials-for-applications-in-flexible-tactile-sensors.

(Continued)

*Primary Examiner* — Christopher Koharski
*Assistant Examiner* — Kaitlyn E Selmer
(74) *Attorney, Agent, or Firm* — Schott, P.C.

(57) ABSTRACT

An ultrasound device comprises a transducer arrangement and an acoustically transmissive window over said arrangement, said window comprising an elastomer layer having conductive particles dispersed in the elastomer, the elastomer layer having a pressure-sensitive conductivity. An electroactive material actuator is provided for biasing the transducer arrangement towards the transmissive window. The electroactive material actuator is controlled in dependence on a measured pressure-sensitive conductivity. In this way, a feedback system is provided for controlling a contact (Continued)

pressure. The device can be implemented with low cost and with low power consumption.

18 Claims, 3 Drawing Sheets

(56) References Cited

U.S. PATENT DOCUMENTS

| | | | |
|---|---|---|---|
| 6,283,919 B1 | 9/2001 | Roundhill et al. | |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 8,328,725 B2 | 12/2012 | Anthony et al. | |
| 2004/0012383 A1* | 1/2004 | Kimura | G01R 1/07371 324/763.01 |
| 2004/0236223 A1* | 11/2004 | Barnes | A61B 8/04 600/459 |
| 2009/0001855 A1 | 1/2009 | Lipton et al. | |
| 2010/0016727 A1 | 1/2010 | Rosenberg | |
| 2013/0017367 A1* | 1/2013 | Ravagnan | C23C 14/22 428/144 |
| 2014/0265728 A1* | 9/2014 | Li | G01N 29/06 310/321 |
| 2015/0272544 A1 | 10/2015 | Raum et al. | |
| 2016/0025669 A1* | 1/2016 | Sun | G01N 27/305 205/790.5 |
| 2016/0089111 A1* | 3/2016 | Yamada | B06B 1/0629 600/459 |
| 2017/0333223 A1* | 11/2017 | Rasmussen | A61F 2/80 |
| 2017/0347957 A1* | 12/2017 | van den Ende | A61B 5/02438 |
| 2018/0065148 A1* | 3/2018 | Beckers | G01S 15/02 |

OTHER PUBLICATIONS

Search Report dated Jan. 4, 2018.
O. Oralkan et al. "Capacitive Micromachined Ultrasonic Transducers: next Gneration Arrays for Acoustic Imaging" IEEE Transactions on UFFC, vol. 49, Nov. 2002.

* cited by examiner

ULTRASOUND DEVICE CONTACTING

CROSS-REFERENCE TO PRIOR APPLICATIONS

This application is the U.S. National Phase application under 35 U.S.C. § 371 of International Application No. PCT/EP2017/078518, filed on Nov. 8, 2017, which claims the benefit of EP Patent Application No. EP 16198779.7, filed on Nov. 15, 2016. These applications are hereby incorporated by reference herein.

FIELD OF THE INVENTION

The present invention relates to an ultrasound device comprising a transducer arrangement for application to the skin.

BACKGROUND OF THE INVENTION

Ultrasound waves find several applications in medicine. One such application is ultrasound imaging, wherein ultrasound waves are emitted by an ultrasound device comprising an array of ultrasound transducers into the body of a patient and echoes of the ultrasound waves are collected by the ultrasound transducers or by dedicated ultrasound receivers and processed to generate an ultrasound image, e.g. a 1D, 2D or 3D ultrasound image. Another application is ultrasound therapy such as high intensity focused ultrasound (HIFU) therapy in which ultrasound beams are generated by an ultrasound device comprising ultrasound transducer element tiles and are focused on diseased tissue. The significant energy deposition at the focus creates local temperatures in the range of about 65° C. to 85° C., which destroys the deceased tissue by coagulative necrosis.

Such applications face several challenges. For instance, in imaging applications it is far from trivial to achieve a good contact between the ultrasound transducer array and the part of the body to be imaged. The contact pressure is critical in ultrasound imaging procedures. A very low pressure or no contact results in poor acoustic coupling. A high contact pressure leads to discomfort, safety issues or impact/mechanical damage. Appropriate contact is typically achieved by using special gels that improve the contact between the ultrasound transducer array and the body part. However, a drawback of this approach is that usually large amounts of gel have to be used, which may contain air bubbles that interfere with the transmission or reception of the ultrasound signals. Moreover, the ultrasound transducer array, e.g. in the form of the probe, is typically hand-held during an imaging procedure, which makes the procedure prone to errors. In addition, there are instances where a hand-held solution is not viable, such as for example when imaging is performed from locations inside the body. This for example applies to large area ultrasound transducers (e.g. wearable US patches) and transesophageal echocardiogram (TEE) probes, where it is notoriously difficult to establish a good contact between the ultrasound transducers and the body region to be imaged or treated. Manual manipulation of ultrasound probes is also difficult when imaging is done as part of monitoring over a longer periods of time such as for example longer than hours, either continuously or with multiple imaging instances distributed during the monitoring time.

Similar challenges exist in therapeutic applications, where the focused beam requires periodic readjustment to treat multiple regions of the diseased tissue. This may be done manually by adjusting a focusing element tile or by beam steering by adjustment of the relative phases of the signals generated by the respective ultrasound transducer elements. The manual adjustment is prone to inaccuracies and the range of phase controlled beam steering may not be sufficient to reach all diseased tissue without array displacement.

There exists a need to assess the quality of the contact between the ultrasound transducer array and a body to be subjected to the ultrasound waves produced with the ultrasound transducer array, such that suboptimal operation of the ultrasound device due to a poor quality conformal contact between the ultrasound transducer array and the body can be avoided or rectified.

SUMMARY OF THE INVENTION

The present invention seeks to provide an ultrasound system including such an ultrasound device, in which the ultrasound system is adapted to adjust the contact pressure in response to a quality assessment of the contact between the transducer arrangement and a body to be subjected to the ultrasound waves produced with the transducer arrangement as provided by the ultrasound device.

The disclosure provides an ultrasound device comprising:
a transducer arrangement;
an acoustically transmissive window over said arrangement, said window comprising an elastomer layer having conductive particles dispersed in the elastomer, the elastomer layer having a pressure-sensitive conductivity;
an electrode arrangement coupled to said elastomer layer and adapted to enable measurement of said pressure-sensitive conductivity;
an electroactive material actuator for biasing the transducer arrangement towards the transmissive window; and
a controller for controlling the electroactive material actuator in dependence on the measured pressure-sensitive conductivity.

This device provides sensing of the contact pressure between an ultrasound transducer and the surface (i.e. skin) to which it is applied. This is done via the acoustically transmissive window that has a pressure sensitive electrical conductivity. When the window is brought in contact with the body to be measured and thus experiences a defined contact pressure, the conductivity can be measured and the value used to determine or represent the contact pressure. This sensed conductivity or the contact pressure it represents is used as a feedback parameter for controlling (actuating) an electroactive material actuator in such a way as to bias or urge the transducer towards the skin. This can be for reestablishing contact between the transducer and the body to be measured if contact had been lost and/or for increasing contact pressure with this body if it dropped below a predefined threshold. Hence in this way the feedback control loop is completed.

The transducer arrangement is mechanically coupled to the transmissive window. In this way the biasing of the actuator can be transmitted to the transmissive window, which is to contact the body to be investigated. This mechanical coupling can be and preferably is a direct coupling in which the transducer arrangement is in contact with the transmissive window. Alternatively, this can be via intermediate layers or bodies that may be part of the transmissive window or not. Such layers must also be capable of transmitting the ultrasound radiation from the transducer arrangement to the body to be investigated.

The controller is thus also for measuring the electrical pressure sensitive conductivity. The controller preferably is configured for measuring the conductivity at multiple times at predetermined time intervals which may be regular intervals or irregular intervals.

The device preferably is also capable of reducing the contact pressure if it becomes too high. An actuation level may then be reduced to a desired level. The same feedback loop can be used for this. The controller can also be configured to provide this function. A biased spring opposing the actuation caused biasing can be used to aid the reduction of pressure when actuation is lessened. Some actuators may be slow in switching from high to lower level of actuation and the spring may aid to increase the switching and thus feedback speed. Even a further actuator that opposes the one for increasing the contact pressure can be used for this in combination with appropriate feedback and control by the controller. The actuators can be used as antagonists.

Thus, a pressure sensitive ultrasound acoustic window is combined with an electro active material actuator to provide an ultrasound tissue contact control system. The window can be optimized for acoustic impedance, attenuation as well as pressure sensitivity. During on/in body ultrasound procedures the body contact pressure can be measured and controlled.

An important advantage of the configuration is that it allows measurement of the contact pressure where it is most relevant, namely at the location where ultrasound imaging takes place. The pressure is measured at a contact point between body and ultrasound transducer and the ultrasound waves travel at least locally through the sensor effectively. The type of pressure sensor used allows adjustment or optimisation of the ultrasound transmissivity such that it can be acoustically matched at least to some extent to the body to be investigated, thus providing capability of reduction of interference of the sensor with the ultrasound measurements. Contact pressure measurement using pressure sensors located next to the ultrasound transducer arrangement or device do not provide this advantage and consequently are less precise. The device can be implemented with low cost and with low power consumption.

Contact pressure is particularly relevant for in body applications, such as for procedures involving the esophagus, lungs etc. whereas acoustic coupling is particularly relevant for on-body applications.

The invention may for example be used during minimum invasive procedures or for wearable ultrasound applications. If there is no contact detected by the pressure sensing, the ultrasound transducer can be switched off thereby increasing lifetime.

For some applications, the elastomer layer may have an acoustic impedance that is matched to the acoustic impedance of a body to be exposed to the ultrasound waves produced by the ultrasound device and/or to the acoustic impedance of the transducer arrangement. This ensures an efficient acoustic coupling between the elastomer layer and the body and/or transducer arrangement, thereby minimizing losses of ultrasound waves, e.g. through reflection. The body may be a human or animal body and the matching is then towards such body.

In an embodiment, the acoustic impedance of the elastomer layer is in the range of 1.3-3.0 MRayls, preferably wherein the acoustic impedance is in the range of 1.3-1.9 MRayls. This for example makes the elastomer layer particularly suited for use with e.g. piezoelectric transducer elements and capacitive micro-machined ultrasonic transducer CMUT) elements, with the latter transducer elements being particularly well-matched to a elastomer layer having an acoustic impedance in the range of 1.3-1.9 MRayls.

The transducer arrangement is typically adapted to generate ultrasound waves having a minimum wavelength in a body to be exposed to the ultrasound waves produced. Preferably, the conductive particles have a maximum diameter of less than 10% of said minimum wavelength in order to minimize reflections or scattering of the ultrasound waves by the conductive particles.

The elastomer may be a polyolefin, a diene polymer or a polysiloxane, a co-polymer or block-copolymer comprising a polyolefin, a diene polymer or a polysiloxane or a blend thereof, preferably wherein the elastomer is polybutadiene or polydimethylsiloxane (PDMS). Such elastomers exhibit the desired elastomer properties at the typical temperatures at which the body is exposed to the ultrasound waves, e.g. at room temperature or body temperature of the patient's body, as well as exhibit acoustic impedances that can be tuned by the inclusion of conductive particles to achieve a desirable acoustic impedance below the percolation threshold of the elastomer.

The conductive particles may be any suitable type of conductive particles such as carbon particles, carbon composite particles, ceramic particles, metal particles, metal alloy particles, composite metal particles and conductive metal oxide particles or combinations thereof. The conductive particles or a combination of conductive particles may be selected on the basis of the desired acoustic functionality of the pressure-sensitive elastomer layer, e.g. to tune the acoustic impedance of the pressure-sensitive elastomer layer.

In an embodiment, the elastomer layer comprises a mixture of electrically conductive particles and non-conductive particles. The inclusion of non-conductive (electrically insulating) particles may facilitate an increase in the acoustic impedance of the elastomer layer.

In an embodiment, the volume of the conductive particles in the elastomer layer is at least 15% by volume based on the total volume of the elastomer layer. It has been found that regardless of the nature of the conductive particles, the elastomer layers have good pressure sensitivity if the amount of conductive particles in the elastomer layer is at least 15% by volume but below the percolation threshold of the elastomer layer for an elastomer layer in which conductive paths are formed by applying pressure to the elastomer layer or above the percolation threshold of the elastomer layer for an elastomer layer in which conductive paths are broken by applying pressure to the elastomer layer.

The elastomer layer may have a thickness in the range of 10-200 µm in at least some of the embodiments. It has been found that an elastomer layer having a thickness in this range exhibits a strong conductive response to applied pressure whilst at the same time causing minimal losses of ultrasound waves transmitted by the transducer arrangement through the acoustically transmissive window. In an embodiment, the elastomer layer may form part of an impedance matching layer and may be implemented as a $\lambda/4$ layer in which $\lambda$ is the wavelength of the ultrasound waves travelling through the elastomer layer. Depending of the typical wavelengths of the applied ultrasound waves, such an elastomer layer may have a thickness in the range of 10-100 µm.

In some embodiments, the elastomer layer is sandwiched in between the electrode arrangement. In a particularly advantageous embodiment, the electrode arrangement comprises an electrode matrix arranged to measure the pressure-sensitive conductivity of individual portions of the elastomer layer. In this embodiment, particularly fine-grained information regarding the quality of the contact between the ultrasound device and the body to be exposed to the ultrasound waves can be obtained, due to the fact that for each electrode cell of the electrode matrix such contact information may be independently obtained. The elastomer layer may be a continuous layer or may be a patterned layer in this embodiment, with the patterned layer comprising a plurality of elastomer layer portions, each of said portions being arranged within one of the cells of the electrode matrix.

The electroactive material actuator can comprise a plurality of individually controllable electroactive material actuators, the different actuators of the plurality of electroactive material actuators being controlled in dependence of the pressure sensitive conductivity measured by different individual portions of the elastomer layer. Preferably the actuators are for biasing the transducer at the location of the portion of the elastomer layer where it receives its conductivity/pressure feedback from.

The ultrasound device can thus comprise at least a second electroactive material actuator, wherein the controller is adapted to control the first and second electroactive material actuators to implement a contact pressure profile. The pressure feedback for the first and second actuator may thus come from different portions of the elastomer layer.

Each electroactive material actuator can comprise an electroactive polymer actuator. This may be one of the plurality of actuators referred to hereinabove.

The acoustically transmissive window may further comprise a further elastomer layer having electrically conductive particles and optionally electrically insulating particles dispersed therein, the elastomer layer having a temperature-sensitive electrical conductivity, the ultrasound device further comprising a further electrode arrangement coupled to said further elastomer layer adapted to measure said temperature-sensitive conductivity. Such a further elastomer layer may be independently optimized to provide temperature information in addition to the pressure information provided by the elastomer layer. Such temperature information for example may be used to measure the quality of the contact between the ultrasound device and the patient's body and/or to prevent overheating of the ultrasound device.

BRIEF DESCRIPTION OF THE DRAWINGS

Examples of the invention will now be described in detail with reference to the accompanying drawings, in which.

It should be understood that the Figures are merely schematic and are not drawn to scale. It should also be understood that the same reference numerals are used throughout the Figures to indicate the same or similar parts.

DETAILED DESCRIPTION OF THE EMBODIMENTS

In the context of the present application, the term 'conductive' means 'electrically conductive' unless explicitly stated otherwise. Similarly, the term 'non-conductive' means 'electrically insulating' unless explicitly stated otherwise. Instead of conductivity, resistivity can be measured. This is considered equivalent as both conductivity and resistivity are parameters for indicating the extent to which a material is capable of conducting current.

The feedback signal may be in the form of a current value measured or a voltage parameter measured. Likewise a resistivity or conductivity value may be calculated from voltage and current measurements.

The invention makes use of an actuator using an electroactive material (EAM), This is a class of materials within the field of electrically responsive materials. When implemented in an actuation device, subjecting an EAM to an electrical drive signal can make them change in size and/or shape. This effect can be used for actuation and sensing purposes. During the actuation the output of such actuators can be in the form of stroke and/or strain such as a force or bias, or a pressure.

There exist inorganic and organic EAMs.

A special kind of organic EAMs are Electroactive polymers (EAPs), some of which are also referred to as electrically responsive materials. They can also work as sensors or actuators, but can be more easily manufactured into various shapes allowing easy integration into a large variety of systems when compared to their inorganic counterparts. Other advantages of EAPs include low power, small form factor, flexibility, noiseless operation, and accuracy, the possibility of high resolution, fast response times, and cyclic actuation. An EAP device can be used in any application in which a small amount of movement of a component or feature is desired, based on electric actuation. Similarly, the technology can be used for sensing small movements. The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-20 kHz.

Figure 1:
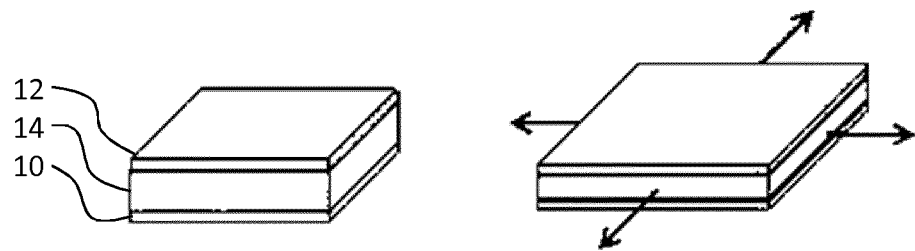
FIG. 1 shows an electroactive material device which is not clamped to a carrier layer.
Figure 2:
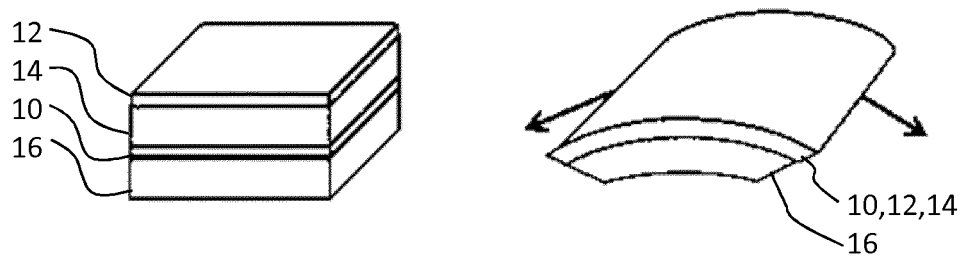
FIG. 2 shows an electroactive material device which is designed so that the expansion arises only in one direction.

As an example of how an EAM device can be constructed and can operate, FIGS. 1 and 2 show two possible operating modes for an EAP device that comprises an electroactive polymer layer 14 sandwiched between electrodes 10, 12 on opposite sides of the electroactive polymer layer 14.

FIG. 1 shows a device which is not clamped to a carrier layer. A voltage is used to cause the electroactive polymer layer to expand in all directions as shown.

FIG. 2 shows a device which is designed so that the expansion arises only in one direction. To this end the structure of FIG. 1 is clamped or attached to a carrier layer 16. A voltage is used to cause the electroactive polymer layer to curve or bow. The nature of this movement arises from the interaction between the active layer which expands when actuated, and the passive carrier layer which does not.

It is noted that actuators based on inorganic EAM can also be made and operated as described for the EAP devices with respect to FIGS. 1 and 2.

Figure 3:
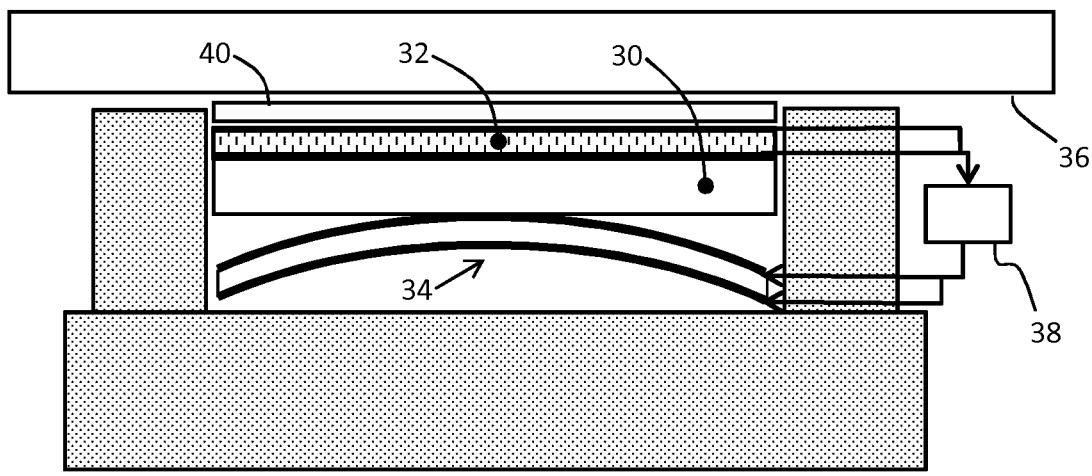
FIG. 3 shows an ultrasound device.

FIG. 3 shows an ultrasound device comprising a transducer arrangement 30 and an acoustically transmissive window 32 over said transducer arrangement. The window 32 comprises an elastomer layer having conductive particles dispersed in the elastomer of the layer, the elastomer layer having a pressure-sensitive conductivity. An electrode arrangement coupled to the elastomer layer is adapted to provide signals to enable measurement of the pressure-sensitive conductivity.

The device further comprises an electroactive material actuator 34 for biasing the transducer arrangement 30 towards the transmissive window 32, thereby urging the transmissive window 32 against a body 36, such as the skin of a patient being examined. The contact with the body is with the transmissive window which is between the transducer arrangement and the body. A controller 38 is provided for controlling the electroactive material actuator in dependence on the measured pressure-sensitive conductivity. The controller is thus adapted to receive from the electrodes and/or apply to the electrodes signals needed to measure the pressure sensitive conductivity or resistivity and, if necessary, manipulate the sensed signals before providing feedback to the actuator.

In the example shown, the electroactive material layer is constrained laterally in a holder so that the displacement is in a normal direction. The holder thus converts lateral expansion into bending and hence application of a normal force. The configuration with a backing layer as described with reference to FIG. 2 may also be used, even without the constriction. Other geometric arrangements are possible, for example with the expansion in the direction in which force is to be applied, rather than perpendicularly as in the example of FIG. 3.

In this example the actuator provides biasing to the bottom part of the transducer arrangement which transfers this to the transmissive window that is in mechanical contact with the top part of the transducer arrangement. Other mechanical couplings between the transducer arrangement and the window can be used. For example the actuator or a plurality of them may be located at the side of the transducer. The actuator may be arranged to push a lever assembly or spring to transmit its biasing to the window. Many other configurations may be used, but they all use the same principle based on the local contact pressure measurement and its use as feedback to control the contact pressure again.

There may be more than one of such actuators in one device distributed over the area beneath the transducer. They preferably are individually controllable (can be independently actuated). This enables a more local contact pressure variation and control, especially if contact pressure feedback to each of the individual actuators is from individual ones of a plurality of portions of the transmissive window. The feedback from each of the actuators then preferably comes from a portion of the window directly between the actuator that is fed back with its conductivity data and the body part with which that portion is in contact. One could also think of such device as having multiple of the devices of FIG. 3 next to each other in one ultrasound device/system. The controllers may be separate or combine in one. Plurality of portions of the window and actuators can be arranged in arrays with rows and columns.

In one possible example, a fixed contact pressure level is set either automatically or by a user and the actual contact pressure is regulated that to that level by the controller. The set pressure levels may be equal over the complete transducer if a matrix pressure sensor and multiple actuators (or actuator segments) are used, but they may be different if a contact pressure gradient along a body surface is needed. The set values can be varied over time.

For example at a first time instance a first set of ultrasound imaging conditions is needed while in a later stage another set of such conditions is needed. Thus, it is possible to increase or reduce a set pressure value, provide regulation at this level, for example depending on image quality or comfort or position on the body or patient specific (skin) parameters.

Typical examples of the regulated pressure levels may be 0.01 to 0.1 $N/cm^2$, but other pressure levels are equally possible depending on the application.

An overall ultrasound system may comprise a plurality of ultrasound transducer tiles each as shown in FIG. 3 on a carrier, forming an array.

The ultrasound transducer arrangement 30 may comprise one or more elements such as piezoelectric transducer elements or CMUT elements, where CMUT stands for Capacitive micromachined ultrasonic transducers. CMUTs are the transducers where the energy transduction is due to change in capacitance. CMUTs are constructed on silicon using micromachining techniques. A cavity is formed in a silicon substrate, and a thin layer suspended on the top of the cavity serves as a membrane on which a metallized layer acts an electrode, together with the silicon substrate which serves as a bottom electrode. If an AC signal is applied across the biased electrodes, the vibrating membrane will produce ultrasonic waves in the medium of interest. In this way it works as a transmitter. On the other hand, if ultrasonic waves are applied on the membrane of a biased CMUT, it will generate alternating signal as the capacitance of the CMUT is varied. In this way, it works as a receiver of ultrasonic waves. More detailed description is found in literature such as General Description and Advantages of CMUTs". Stanford University. Archived from the original on 20 Jul. 2011. Retrieved 7 Feb. 2011, or "Capacitive Micromachined Ultrasonic Transducers: Next-Generation Arrays for Acoustic Imaging" (PDF). IEEE Transactions on UFFC, Vol. 49, published November 2002 and references therein.

In a particularly preferred embodiment, the ultrasound system comprises a plurality of CMUT tiles. The individual CMUT elements on each tile are for example arranged to be operated in a so-called collapse mode as will be explained in further detail below.

The ultrasound transducer arrangement 30 transmits ultrasound waves through the acoustic transmissive window 32 which is acoustically coupled to the transducer arrangement 30, namely to the transmitting surface of the ultrasound transducer elements or elements of the transducer arrangement 30. The acoustic window 32 protects the transducer arrangement from being directly contactable, thereby protecting the transducer arrangement from damage, as well as protecting the body to be exposed to the ultrasound waves to be generated by the transducer array from being directly contacted by the transducer array, e.g. to protect the body from accidental electrical shock.

The transmissive window further provides impedance matching between the transducer array and the body.

The transmissive window 32 comprises an elastomer layer having conductive particles dispersed in the elastomer layer to impart pressure-sensitive conductivity onto the elastomer layer. The elastomer provides an electrically insulating matrix for the conductive particles. The conductive particles are present in a concentration in the elastomer below the percolation threshold of the elastomer, i.e. below the limit at which the conductive particles form permanent conductive pathways through the elastomer layer, i.e. are in permanent contact with each other. Instead, such conductive pathways are temporarily formed by the application of a pressure on the elastomer layer, thus causing a change, e.g. a decrease, in the electrical resistance of the elastomer layer. A change in the applied pressure to the elastomer layer typically causes a change in the number and/or length of the conductive pathways formed by the conductive particles through the elastomer layer, such that a change in pressure applied to the elastomer layer typically causes a change in the electrical resistance of this layer.

Therefore, the electrical resistance of the elastomer layer provides an indication of the contact between the transducer arrangement of the ultrasound device and a surface brought into contact with the transmissive window, e.g. part of a body of a patient to be exposed to the ultrasound waves.

Alternatively, the conductive particles may be present in a concentration in the elastomer above the percolation threshold of the elastomer, i.e. above the limit at which the conductive particles form permanent conductive pathways through the elastomer layer, i.e. are in permanent contact with each other. In this embodiment, such conductive pathways are temporarily disrupted by the application of a pressure on the elastomer layer, thus causing a change, e.g. an increase, in the electrical resistance of the elastomer layer.

In order to achieve good pressure sensitivity in the elastomer layer, the concentration of the conductive particles in the elastomer layer preferably is at least 15% by volume based on the total volume of the elastomer layer and more preferably is close to the percolation threshold of the elastomer, e.g. below or above the percolation threshold, to maximize piezoelectric sensitivity of the elastomer, e.g. the concentration of the conductive particles in the elastomer layer may be 15-25% by volume based on the total volume of the elastomer layer.

The elastomer layer preferably is acoustically matched to the acoustic impedance of the transducer array, i.e. has an acoustic impedance that approximately matches the acoustic impedance of the transducer array. For example, in case of the transducer array comprising piezoelectric transducers, the elastomer layer may have an acoustic impedance ranging from 1.3-3.0 MRayls, whereas in case of the transducer array comprising CMUT elements, the elastomer layer may have an acoustic impedance ranging from 1.3-1.9 MRayls, which has the further advantage that the acoustic impedance is closely matched to that of body tissue, which typically has acoustic impedance of about 1.6 MRayls.

In an example embodiment, the elastomer layer has an acoustic impedance ranging from 1.4-1.7 MRayls.

The acoustic impedance of the elastomer layer may be tuned by selection of the elastomer, i.e. by choosing an elastomer having a suitable intrinsic acoustic impedance, which intrinsic acoustic impedance may be adjusted by the inclusion of conductive particles having a further intrinsic acoustic impedance, such that the overall acoustic impedance of the elastomer layer is defined by the combination of the intrinsic acoustic impedance of the elastomer and the further intrinsic acoustic impedance of the conductive particles. A mixture of conductive particles having different intrinsic acoustic impedances may be used for this purpose.

For example, the acoustic impedance of the elastomer layer may be tuned by selecting conductive particles having a particular density and/or size, as the acoustic impedance $Z$ of the particle may be expressed as $Z = v*\rho$, in which v is the speed of sound and $\rho$ is the particle density. Hence, relatively heavy (dense) particles may be used to increase the intrinsic acoustic impedance of the elastomer of the elastomer layer. Any suitable elastomer may be used as the elastomer for the elastomer layer.

For example, the elastomer may be a polyolefin, a diene polymer or a polysiloxane, a co-polymer or block-copolymer comprising a polyolefin, a diene polymer or a polysiloxane or a blend thereof although embodiments are not limited thereto. Polybutadiene, polydimethylsiloxane and relatively soft polyether block amides (PEBA) commonly used in catheters, are specifically mentioned as suitable elastomers.

Any suitable conductive particle may be used in the elastomer layer. For example, the conductive particles may comprise at least one of carbon particles, e.g. graphite or graphene particles, carbon composite particles, ceramic particles, metal particles, metal alloy particles, composite metal particles and conductive metal oxide particles although embodiments are not limited thereto.

In at least some embodiments, the elastomer layer comprises a mixture of conductive particles and non-conductive particles. The inclusion of non-conductive particles may be useful to tune the acoustic impedance of the elastomer layer. For example, the non-conductive particles may be particles having a relatively high density such that a small fraction of non-conductive particles relative to the total fraction of particles (i.e. non-conductive particles+conductive particles) in the elastomer layer can significantly increase the acoustic impedance of the elastomer layer without significantly reducing its piezoelectric sensitivity. Any suitable non-conductive particles or mixture of non-conductive particles may be used for this purpose. By way of non-limiting example, the non-conductive particles may be ceramic particles, e.g. transition metal oxide, nitride, carbide particles, high-density metal oxide, nitride, carbide particles and so on.

In an embodiment, the elastomer layer has a thickness in the range of 10-200 μm, e.g. 150 μm. If the thickness of the elastomer layer exceeds 200 μm, the flexibility of the elastomer layer may deteriorate. If the thickness of the elastomer layer is less than 10 μm, it may be difficult to achieve the desired pressure sensitivity in the elastomer layer.

In a particular embodiment, the pressure sensitive elastomer layer may be a matching layer having a thickness of $\lambda/4$ to prevent reflections of ultrasound waves having a wavelength $\lambda$ passing through the elastomer layer. For example, the propagation speed v of ultrasound waves through PDMS is 1000 m/sec. For ultrasound waves having a frequency f of 10 MHz, $\lambda$, $= v/f = 100$ micron. By choosing the PDMS layer to have a thickness d=25 micron, large scale reflections of the 10 MHz ultrasound waves by the elastomer layer are effectively avoided. From the foregoing, it will be immediately apparent to the skilled person that the thickness d of the elastomer layer may be tuned based on the propagation speed v of ultrasound waves through the elastomer layer as well as based on the major or center frequency f of the ultrasound waves generated by the ultrasound device.

The ultrasound device may be adapted to generate ultrasound waves in a particular wavelength range in the body of the patient. For example, ultrasound waves in the 7-12 MHz range correspond to a wavelength in the body of about 0.1-0.2 mm. The maximum particle size of the conductive particles in the elastomer layer preferably are chosen in accordance with the wavelength range of the ultrasound waves that the ultrasound device can produce in order to minimize reflection of the ultrasound waves emanating from the transducer array (or of ultrasound echoes returning to the ultrasound device). For this reason, the conductive particles and non-conductive particles if present preferably have a maximum diameter of less than 10% of the minimum ultrasound wavelength that can be produced by the ultrasound device.

In the context of the present application, the term 'maximum diameter' refers to the maximum cross-sectional dimension of the (non-)conductive particle, and is not intended to limit the shape of the (non-)conductive particles to spherical particles. The (non-)conductive particles may have any suitable shape, e.g. may be spherical, platelets, flakes, nanoparticles including core-shell nanoparticles, nanowires, nanorods, nanotubes and so on.

The electrode arrangement coupled to the elastomer layer is for example arranged along the periphery of the elastomer layer, i.e. is arranged along at least one edge of the elastomer layer. The controller 38 performs the function of a sensing circuit, which for example applies a voltage potential across the elastomer layer with the electrode arrangement and measures the resulting current running through the elastomer layer. Alternatively, the controller 38 may be arranged to apply a current across the elastomer layer with the electrode arrangement and measure the resulting voltage drop across the elastomer layer to determine its resistivity. Other suitable ways of measuring the piezoelectric resistivity of the elastomer layer will be immediately apparent to the skilled person.

The transmissive window 32 may comprise additional acoustically transparent layers. An optional outer layer 40 is shown in FIG. 3. It may be used to protect the elastomer layer 32 from damage and to protect the patient from accidental electrical shock during electrical conductivity of the elastomer layer.

The outer layer 40 for example may comprise a blend of a thermoplastic polymer selected from a polyolefin family (thermoplastic polyolefin or TPO) and an elastomer selected from a polyolefin family (polyolefin elastomer or POE). Thermoplastic polymers demonstrate plastic elastic behavior and are thermo formable (having the property of softening or fusing when heated and of hardening again when cooled). This formability is reversible, in other words can be repeated as often as required as long as the material is not thermally damaged by overheating. In thermoplastic polyolefin for example, compared to the saturated hydrocarbons, the polyolefin family provides the thermoplastic polymer with a relatively light molecular weight. The introduction of a polyolefin elastomer into a blend of a polyolefin thermoplastic polymer used for an outer layer may provide an increased shear wave attenuation that beneficially reduces crosstalk between the ultrasound transducer elements of different ultrasound transducer tiles. The transmissive window 32 of the ultrasound device may thus include an outer layer formed from a blend of the thermoplastic polyolefin and polyolefin elastomer to achieve a reduction of image artifacts during ultrasound imaging.

An introduction of the polyolefin elastomer into a blend with a thermoplastic polyolefin may change the density of the blend compared to the pure thermoplastic, such that the acoustic impedance of the outer layer may be beneficially adjusted to match the acoustic impedance of the elastomer layer and/or the acoustic impedance of soft tissue (which is about 1.6 MRayls). Other acoustic properties of the outer layer, such as acoustic wave velocity, acoustic energy attenuation and shear wave attenuation, may be also tuned by selecting a different ratio of the elastomer content blended in the thermoplastic polymer. It is desirable to use thermoplastic polyolefin at the outer layer, which may provide mechanical robustness without compromising ultrasound image quality.

An example material for the thermoplastic polymers used in the outer layer 40 is polymethylpentene (poly 4-methyl pentene-1). Polymethylpentene (available from Mitsui under trade name is TPX) material shows a low longitudinal acoustic attenuation. In this context, the longitudinal attenuation corresponds to the wave's amplitude reduction while propagating from the inner surface of the transmissive window 32 arranged to face the transducer array to the outer surface of the acoustic window 32. In a frequency range from 0 up to 10 MHz, polymethylpentene shows an attenuation value below 3 dB/mm for ultrasound frequencies up to 10 MHz.

By providing a temperature sensitive particle filled polymer, temperature protection can be provided. For example, the transducer may be switched off if temperatures rise above an acceptable level. There may be two sensing layers where one is temperature sensitive and the other pressure sensitive or else a single layer may perform both functions.

An inner layer may also be provided between the transducer arrangement and the transmissive window 32. This electrically insulates the transducer array from the elastomer layer.

International patent application with number PCT/EP2017/059907 provides implementations of the transmissive window with pressure sensitive conductivity measurement. It is herewith incorporated by reference. The application provides details for materials, design options and feedback signal measurement which can be used with the device of the current disclosure. Optimisations disclosed in this international application may be used with the device of the current disclosure with similar advantages as described.

The electroactive material actuator 34 is typically based on an electroactive polymer material, although the invention can in fact be used for devices based on other kinds of EAM material. Such other EAM materials are known in the art and the person skilled in the art will know where to find them and how to apply them. A number of options will be described herein below.

A common sub-division of EAM devices is into field-driven and current or charge (ion) driven EAMs. Field-driven EAMs are actuated by an electric field through direct electromechanical coupling, while the actuation mechanism for current or charge driven EAMs involves the diffusion of ions. The latter mechanism is more often found in the corresponding organic EAMs such as EAPs. While field driven EAMs generally are driven with voltage signals and require corresponding voltage drivers/controllers, current driven EAMs generally are driven with current or charge signals sometimes requiring current drivers. Both classes of materials have multiple family members, each having their own advantages and disadvantages.

Field driven EAMs can be organic or inorganic materials and if organic can be single molecule, oligomeric or polymeric. For the current invention they are preferably organic and then also oligomeric or even polymeric. The organic materials and especially polymers are an emerging class of materials of growing interest as they combine the actuation properties with material properties such as light weight, cheap manufacture and easy processing.

The field driven EAMs and thus also EAPs are generally piezoelectric and possibly ferroelectric and thus comprise a spontaneous permanent polarization (dipole moment). Alternatively, they are electrostrictive and thus comprise only a polarization (dipole moment) when driven, but not when not driven. Alternatively they are dielectric relaxor materials. Such polymers include, but are not limited to, the sub-classes: piezoelectric polymers, ferroelectric polymers, electrostrictive polymers, relaxor ferroelectric polymers (such as polyvinylidene fluoride (PVDF) based relaxor polymers or polyurethanes), dielectric elastomers, liquid crystal elastomers. Other examples include electrostrictive graft polymers, electrostrictive paper, electrets, electroviscoelastic elastomers and liquid crystal elastomers.

The lack of a spontaneous polarization means that electrostrictive polymers display little or no hysteretic loss even at very high frequencies of operation. The advantages are however gained at the expense of temperature stability. Relaxors operate best in situations where the temperature can be stabilized to within approximately 10° C. This may seem extremely limiting at first glance, but given that electrostrictors excel at high frequencies and very low driving fields, then the applications tend to be in specialized micro actuators. Temperature stabilization of such small devices is relatively simple and often presents only a minor problem in the overall design and development process.

Relaxor ferroelectric materials can have an electrostrictive constant that is high enough for good practical use, i.e. advantageous for simultaneous sensing and actuation functions. Relaxor ferroelectric materials are non-ferroelectric when zero driving field (i.e. voltage) is applied to them, but become ferroelectric during driving. Hence there is no electromechanical coupling present in the material at non-driving. The electromechanical coupling becomes non-zero when a drive signal is applied and can be measured through applying the small amplitude high frequency signal on top of the drive signal, in accordance with the procedures described above. Relaxor ferroelectric materials, moreover, benefit from a unique combination of high electromechanical coupling at non-zero drive signal and good actuation characteristics.

The most commonly used examples of inorganic relaxor ferroelectric materials are: lead magnesium niobate (PMN), lead magnesium niobate-lead titanate (PMN-PT) and lead lanthanum zirconate titanate (PLZT). But others are known in the art.

PVDF based relaxor ferroelectric based polymers show spontaneous electric polarization and they can be pre-strained for improved performance in the strained direction. They can be any one chosen from the group of materials herein below.

PVDF, Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The current driven EAMs and EAPs comprise conjugated polymers, Ionic Polymer Metal Composites, ionic gels and polymer gels.

Examples of ionic-driven EAPs are conjugated polymers, carbon nanotube (CNT) polymer composites and Ionic Polymer Metal Composites (IPMC).

The sub-class dielectric elastomers includes, but is not limited to:
acrylates, polyurethanes, silicones.

The sub-class conjugated polymers includes, but is not limited to:
polypyrrole, poly-3,4-ethylenedioxythiophene, poly(p-phenylene sulfide), polyanilines.

The materials above can be implanted as pure materials or as materials suspended in matrix materials. Matrix materials can comprise polymers.

To any actuation structure comprising EAM material, additional passive layers may be provided for influencing the behavior of the EAM layer in response to an applied drive signal.

The actuation arrangement or structure of an EAM device can have one or more electrodes for providing the control signal or drive signal to at least a part of the electroactive material. Preferably the arrangement comprises two electrodes. The EAM layer may be sandwiched between two or more electrodes. This sandwiching is needed for an actuator arrangement that comprises an elastomeric dielectric material, as its actuation is among others due to compressive force exerted by the electrodes attracting each other due to a drive signal. The two or more electrodes can also be embedded in the elastomeric dielectric material. Electrodes can be patterned or not.

It is also possible to provide an electrode layer on one side only for example using interdigitated comb electrodes. If electrodes are on one side only, a reflective device may be formed without the need for transparent electrodes.

A substrate can be part of the actuation arrangement. It can be attached to the ensemble of EAP and electrodes between the electrodes or to one of the electrodes on the outside.

The electrodes may be stretchable so that they follow the deformation of the EAM material layer. This is especially advantageous for EAP materials. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminum coating.

The materials for the different layers will be selected for example taking account of the elastic moduli (Young's moduli) of the different layers.

Additional layers to those discussed above may be used to adapt the electrical or mechanical behavior of the device, such as additional polymer layers.

Figure 4:
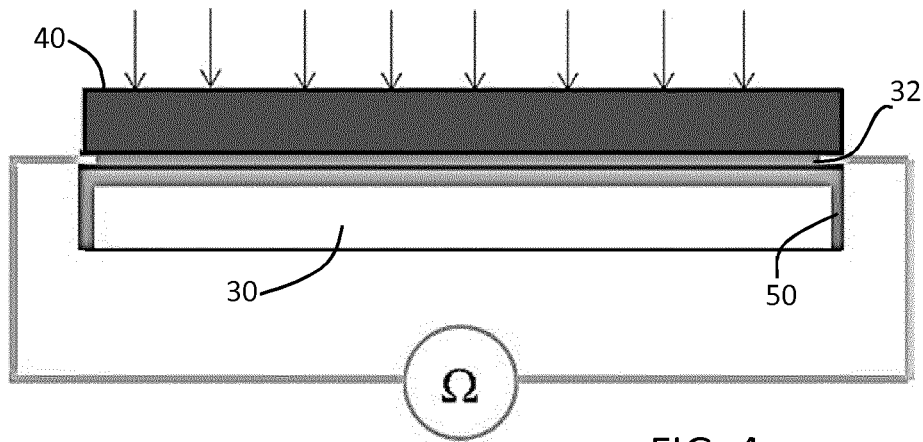
FIG. 4 shows a modification to the device of FIG. 3.

FIG. 4 shows a modification to the device of FIG. 3 having an inner layer 50 between the transducer arrangement 30 and the pressure sensitive layer 32 as well as the top layer 40. This provides a more integrated arrangement.

Figure 5:
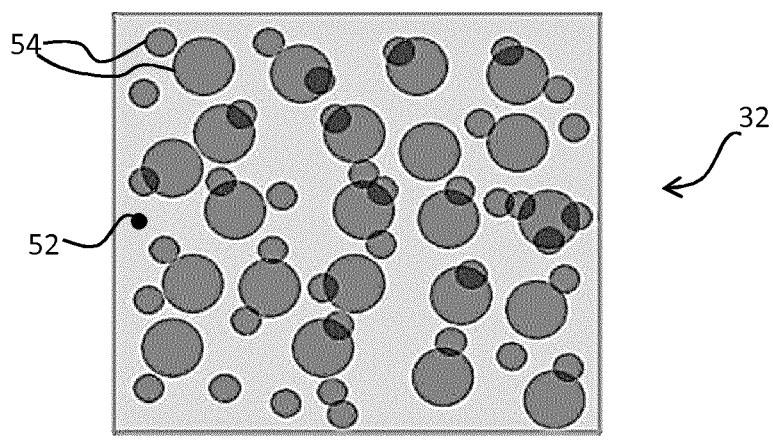
FIG. 5 shows a conductive particle filled polymer.

FIG. 5 shows the conductive particle filled polymer 32. There is an elastomer matrix 52 and conducting particles 54. Depending on the deformation behaviour of the composite, conductive paths are made or broken during deformation causing a positive or negative piezoresistive effect.

Figure 6:
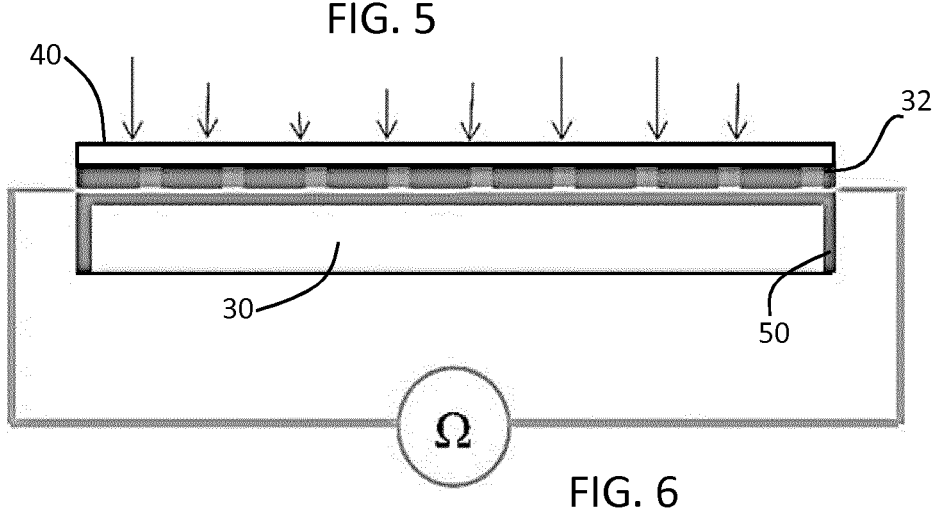
FIG. 6 shows that the pressure sensitive layer may be in the form of a matrix of addressable elements.

FIG. 6 shows that the pressure sensitive layer 32 may be in the form of a matrix of addressable elements, for instance addressed by a thin conductive pattern on a thin foil. The interconnect pattern can also be on top of the acoustic transducer arrangement. In this way a pressure profile over the window (which may be flat or a lens) can be determined.

Figure 7:
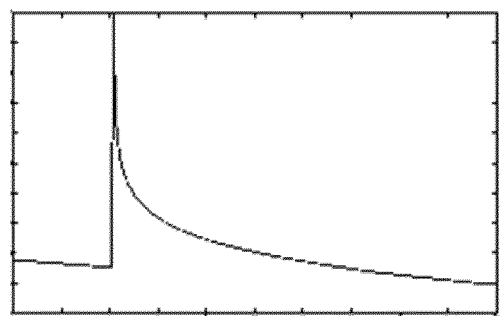
FIG. 7 shows an example of the response of a conductive particle filled polymer.

By way of example, FIG. 7 shows an example of the response of a conductive particle filled polymer (silicone and carbon black) and shows the resistance against time. The pressure sensitive material is gently pressed for a short duration resulting in a resistance peak The conductive particle filled polymer can be optimized for pressure response and also for temperature sensitivity, for sensing the temperature at the transducer arrangement output window. As mentioned above, separate polymers may be used for pressure sensing and temperature sensing.

In the esophagus (TEE, transesophageal echocardiogram) it is difficult to control tissue contact during (long) minimally invasive interventions. The device described above enables an automatic, operator independent tissue contact control system.

There are various possible feedback approaches which can be used.

The electroactive material actuator may itself perform a pressure sensing function in addition to the elastomer layer.

The sensing signal may then comprise the electrical impedance of the EAM measured at a resonance frequency of the EAM device (typically in the order of tens of kHz).

The device may have a second (or further) electroactive material actuator to provide an improved pressure uniformity across the device. In this case, the optimum contact pressure and pressure uniformity across the device can be realized by optimizing the pressure signals applied to both devices.

Pressure sensing signals from the elastomer layer and from the EAM actuator (being operated as a sensing device) can be used to optimize the pressure on the window. The pressure can for example be determined from the elastomer pressure sensor as this may have a higher absolute accuracy, whilst the uniformity can be determined from the two or more EAM actuators by simply using a comparator and feedback to minimize the difference in the sensed pressure signal from these two devices. Such a system would therefore provide two feedback signals; one for absolute pressure and a second for pressure uniformity.

The device can be applied in a wide range of medical ultrasound applications for example (but not limited to) on body, in the esophagus (TEE, transesophageal echocardiogram) wearable ultrasound, large area ultrasound. Different transducer types may be used such as PZT, single crystal, CMUT.

The ultrasound device may be an ultrasound probe or the like for use in an ultrasound imaging system or an ultrasound therapy system. The ultrasound probe may form part of a catheter for invasive imaging or treatment, may form part of a hand-held device for non-invasive imaging or treatment or may form part of a wearable device, e.g. for prolonged treatment of particular area of the body of a patient.

The ultrasound device may form part of an ultrasound system such as an ultrasonic diagnostic imaging system or an ultrasonic therapy system.

Figure 8:
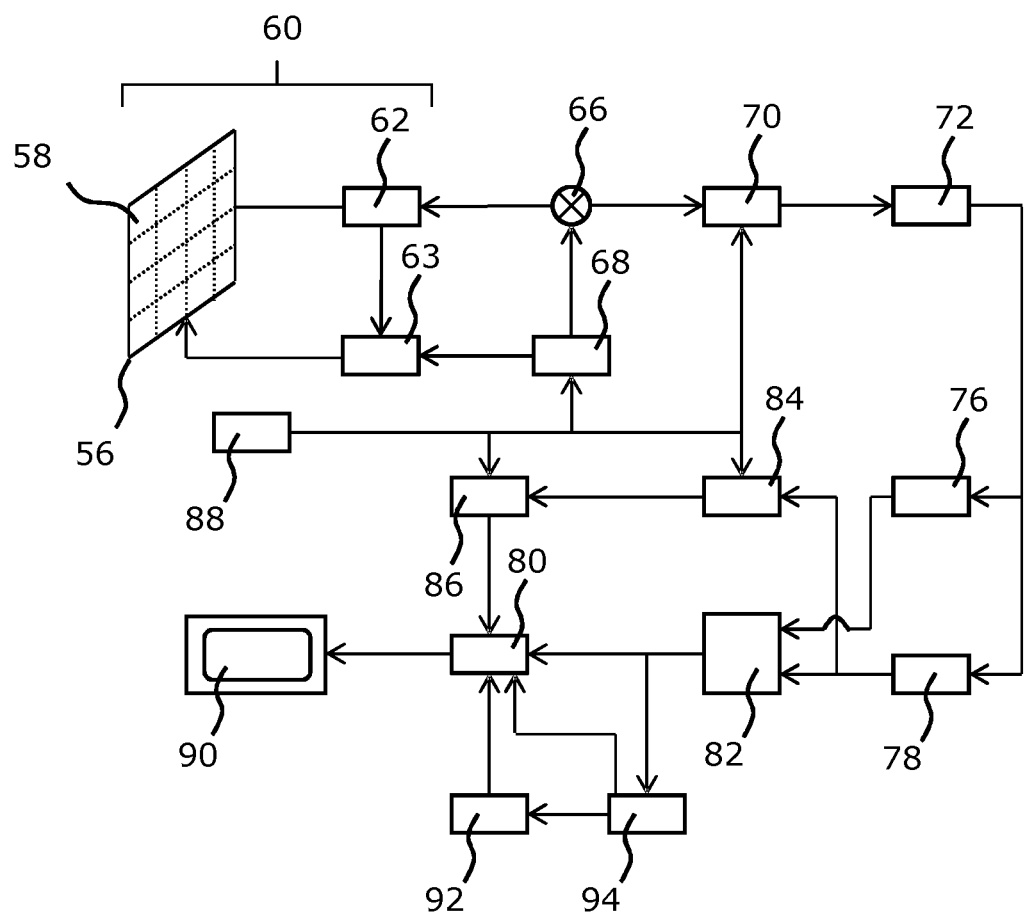
FIG. 8 shows an ultrasound system using the device.

An example embodiment of an ultrasonic diagnostic imaging system is schematically depicted in block diagram form in FIG. 8.

A transducer array 56 comprising the ultrasound transducer tiles 58 is provided in an ultrasound device 60 in the form of a probe for transmitting ultrasonic waves and receiving echo information. The transducer array 56 may be a one- or a two-dimensional array of transducer elements, e.g. tiles 58, capable of scanning in a 2D plane or in three dimensions for 3D imaging.

The transducer array 56 is coupled to a microbeam former 62 in the probe 60 which controls transmission and reception of signals by the array cells, e.g. CMUT cells. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.) The microbeam former 62 is coupled by the probe cable, e.g. coaxial wire, to a transmit/receive (T/R) switch 66 which switches between transmission and reception modes and protects the main beam former 70 from high energy transmit signals when a microbeam former is not present or used and the transducer array 56 is operated directly by the main system beam former 70. The transmission of ultrasonic beams from the transducer array 56 under control of the microbeam former 62 is directed by a transducer controller 68 coupled to the microbeam former by the T/R switch 66 and the main system beam former 70, which receives input from the user's operation of the user interface or control panel 88. One of the functions controlled by the transducer controller 68 is the direction in which beams are steered and focused. Beams may be steered straight ahead from (orthogonal to) the transducer array 56, or at different angles for a wider field of view. The transducer controller 68 is coupled to control a voltage source 63 for the transducer array 56. For instance, the voltage source 63 sets DC and AC bias voltage(s) that are applied to the CMUT cells 58 of a CMUT array 56, e.g. to drive the CMUT cells into a collapse mode.

The partially beam-formed signals produced by the microbeam former 62 are forwarded to the main beam former 70 where partially beam-formed signals from individual patches of transducer elements are combined into a fully beam-formed signal. For example, the main beam former 70 may have 128 channels, each of which receives a partially beam-formed signal from a patch of dozens or hundreds of transducer cells, e.g. from tiles 58. In this way the signals received by thousands of transducer elements of a transducer array 56 can contribute efficiently to a single beam-formed signal.

The beam-formed signals are coupled to a signal processor 72. The signal processor 72 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 72 optionally may perform additional signal enhancement such as speckle reduction, signal compounding, and noise elimination. The bandpass filter in the signal processor 72 may be a tracking filter, with its pass band sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 76 and optionally to a Doppler processor 78. The B-mode processor 76 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 78, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a pass band characteristic which passes signal of relatively low amplitude from higher velocity materials while rejecting relatively strong signals from lower or zero velocity material.

This pass band characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. The structural and motion signals produced by the B-mode (and Doppler) processor(s) are coupled to a scan converter 82 and a multiplanar reformatter 94. The scan converter 82 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 94 will convert echoes which are received from points in a common plane in a volumetric region of the body into an ultrasonic image of that plane, for instance as described in U.S. Pat. No. 6,443,896 (Detmer). A volume renderer 92 converts the echo signals of a 3D data set into a projected 3D image as viewed from a given reference point as described in U.S. Pat. No. 6,530,885 (Entrekin et al.)

The 2D or 3D images are coupled from the scan converter 82, multiplanar reformatter 94, and volume renderer 92 to an image processor 80 for further enhancement, buffering and temporary storage for display on an image display 90. In addition to being used for imaging, the blood flow values produced by the Doppler processor 78 and tissue structure information produced by the B-mode processor 76 are coupled to a quantification processor 84. The quantification processor produces measures of different flow conditions such as the volume rate of blood flow as well as structural measurements such as the sizes of organs and gestational age. The quantification processor may receive input from the user control panel 88, such as the point in the anatomy of an image where a measurement is to be made.

Output data from the quantification processor is coupled to a graphics processor 86 for the reproduction of measurement graphics and values with the image on the display 90. The graphics processor 86 can also generate graphic overlays for display with the ultrasound images. These graphic overlays can contain standard identifying information such as patient name, date and time of the image, imaging parameters, and the like. For these purposes the graphics processor receives input from the user interface 88, such as patient name.

The user interface is also coupled to the transmit controller 68 to control the generation of ultrasound signals from the transducer array 56 and hence the images produced by the transducer array and the ultrasound system. The user interface is also coupled to the multiplanar reformatter 94 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 62 and/or the Doppler processor 78 may be omitted, the ultrasound probe 60 may not have 3D imaging capabilities and so on. Other variations will be apparent to the skilled person.

Moreover, in case of an ultrasonic therapy system, there obviously is no need for the system to be able to receive and process pulse echoes, such that it will be immediately apparent to the skilled person that the above embodiment of an ultrasonic diagnostic imaging system may be adapted to form an ultrasonic therapy system by omission of those system components that are required for the reception of processing of such pulse echoes.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound device comprising:
 a transducer arrangement;
 an acoustically transmissive window disposed over the transducer arrangement,
  wherein the acoustically transmissive window comprises a first elastomer layer,
  wherein the first elastomer layer has conductive particles dispersed in an elastomer material,
  wherein the first elastomer layer has a pressure-sensitive conductivity, and
  wherein the acoustically transmissive window is arranged to determine a contact pressure between the transducer arrangement and a body to be exposed to ultrasound waves produced by the ultrasound device, based on the pressure-sensitive conductivity;
 a first electrode arrangement coupled to the first elastomer layer, wherein the first electrode arrangement is arranged to enable measurement of the pressure-sensitive conductivity;
 a first electroactive material actuator arranged to bias the transducer arrangement towards the acoustically transmissive window; and
 a controller circuit arranged to control the first electroactive material actuator in dependence on the measured pressure-sensitive conductivity.

2. The ultrasound device of claim 1,
 wherein the first elastomer layer has an acoustic impedance that is matched to an acoustic impedance of the body.

3. The ultrasound device of claim 1, wherein an acoustic impedance of the first elastomer layer is in a range of 1.3-3.0 MRayls.

4. The ultrasound device of claim 1, wherein the transducer arrangement is adapted to generate the ultrasound waves having a minimum wavelength in the body to be exposed to the ultrasound waves, the conductive particles having a maximum diameter of less than 10% of the minimum wavelength.

5. The ultrasound device of claim 1, wherein the elastomer material is selected from the group consisting of a polyolefin, a diene polymer or a polysiloxane, a co-polymer or a block-copolymer comprising a polyolefin, a diene polymer, and a polysiloxane.

6. The ultrasound device of claim 1, wherein the conductive particles comprise at least one of: carbon particles, carbon composite particles, ceramic particles, metal particles, metal alloy particles, composite metal particles, and conductive metal oxide particles.

7. The ultrasound device of claim 1, wherein the volume of the conductive particles in the first elastomer layer is at least 15% of a total volume of the first elastomer layer.

8. The ultrasound device of claim 1, wherein the first elastomer layer is sandwiched in between the first electrode arrangement.

9. The ultrasound device of claim 8,
wherein the first electrode arrangement comprises an electrode matrix, and
wherein the electrode matrix is arranged to measure the pressure-sensitive conductivity of individual portions of the first elastomer layer.

10. The ultrasound device of claim 1,
wherein the acoustically transmissive window comprises a second elastomer layer,
wherein the second elastomer layer has conductive particles dispersed therein,
wherein the second elastomer layer has a temperature-sensitive conductivity,
wherein the ultrasound device further comprises a second electrode arrangement coupled to the second elastomer layer, and
wherein the second elastomer layer is arranged to measure the temperature-sensitive conductivity.

11. The ultrasound device of claim 1, wherein the controller circuit is arranged to operate the first electroactive material actuator for pressure sensing.

12. The ultrasound device of claim 1, further comprising at least a second electroactive material actuator, wherein the controller circuit is arranged to control the first electroactive material actuator and the second electroactive material actuators to implement a pressure profile.

13. The ultrasound device of claim 12, wherein each of the first electroactive material actuator and the second electroactive material actuator comprises an electroactive polymer actuator.

14. The ultrasound device of claim 1,
wherein the first elastomer layer has an acoustic impedance that is matched to an acoustic impedance of the body, and
wherein the body is arranged to be exposed to the acoustic impedance of the transducer arrangement.

15. The ultrasound device of claim 1, wherein an acoustic impedance of the first elastomer layer is in a range of 1.3-1.9 MRayls.

16. The ultrasound device of claim 1,
wherein the first elastomer layer is a blend of materials, and
wherein the blend of materials are selected from the group consisting of a polyolefin, a diene polymer or a polysiloxane, a co-polymer or a block-copolymer comprising a polyolefin, a diene polymer, and a polysiloxane.

17. The ultrasound device of claim 1, wherein a concentration of the conductive particles dispersed in the elastomer material is based on a percolation threshold of the elastomer material.

18. The ultrasound device of claim 1, wherein a change in the contact pressure between the transducer arrangement and the body is indicated by a change in electrical resistance of the first elastomer layer.

* * * * *